United States Patent [19]

Foster, Jr.

[11] Patent Number: 4,485,805
[45] Date of Patent: Dec. 4, 1984

[54] WEIGHT LOSS DEVICE AND METHOD

[75] Inventor: Lawrence H. Foster, Jr., Zephyr Cove, Nev.

[73] Assignee: Gunther Pacific Limited of Hong Kong, Central, Hong Kong

[21] Appl. No.: 411,053

[22] Filed: Aug. 24, 1982

[51] Int. Cl.$^3$ .............................................. A61B 17/00
[52] U.S. Cl. .................................. 128/1 R; 128/344; 604/54; 604/96
[58] Field of Search ..................... 604/49, 54, 96–100; 128/1 R, 325, 344, 303 R

[56] References Cited

U.S. PATENT DOCUMENTS

| 4,133,315 | 1/1979 | Berman | 128/344 X |
| 4,236,521 | 12/1980 | Lauterjung | 604/270 |
| 4,416,267 | 11/1983 | Garren et al. | 128/1 R |

FOREIGN PATENT DOCUMENTS

| 2822925 | 11/1979 | Fed. Rep. of Germany | 128/344 |
| WO80/00007 | 1/1980 | PCT Int'l Appl. | 128/344 |
| 2090747 | 7/1982 | United Kingdom | 128/344 |

Primary Examiner—Dalton L. Truluck
Attorney, Agent, or Firm—John W. Huckert

[57] ABSTRACT

The intra-gastric weight loss system apparatus and method of the present invention includes an intra-gastric elastomeric rubber balloon with self-sealing fill valve, to be placed and retrieved without surgery. As a benign space-occupying device, it will decrease gastric capacity to the point that saiety (the feeling of fullness) will occur after very little food has been consumed. Thus, the advantages of gastric and intestinal by-pass surgery will be realized, without surgery and the many resulting complications thereof. The elastomeric balloon is inflated with a liquid, preferably a saline solution containing an X-ray contrast media. The balloon is placed in a person's stomach by passing a naso-gastric tube through the mouth. The N-G tube has a previously placed nylon pull string through the lumen and back up the exterior. After this, a metal stylette is run down the lumen to very near the end of the N-G tube. The rolled up balloon with fill tube attached is inserted into a rubber finger cot attached to the pull string. By pulling the string the balloon containing finger cot is drawn down into the stomach. After placement in the stomach the stylette is removed and the balloon is inflated with liquid. Inflation causes the rubber finger cot to roll up and remove itself. Then the fill tube is withdrawn and the pull string with the finger cot attached is withdrawn. The balloon is now free-floating in the person's stomach without any tube attached. Regular check-ups, administration of food supplements, etc., follow thereafter. When the desired weight loss has been achieved the balloon can be easily deflated, and passed in normal fashion, or removed by use of a gastroscope and snaring of an attached withdrawal loop on the balloon.

5 Claims, 4 Drawing Figures

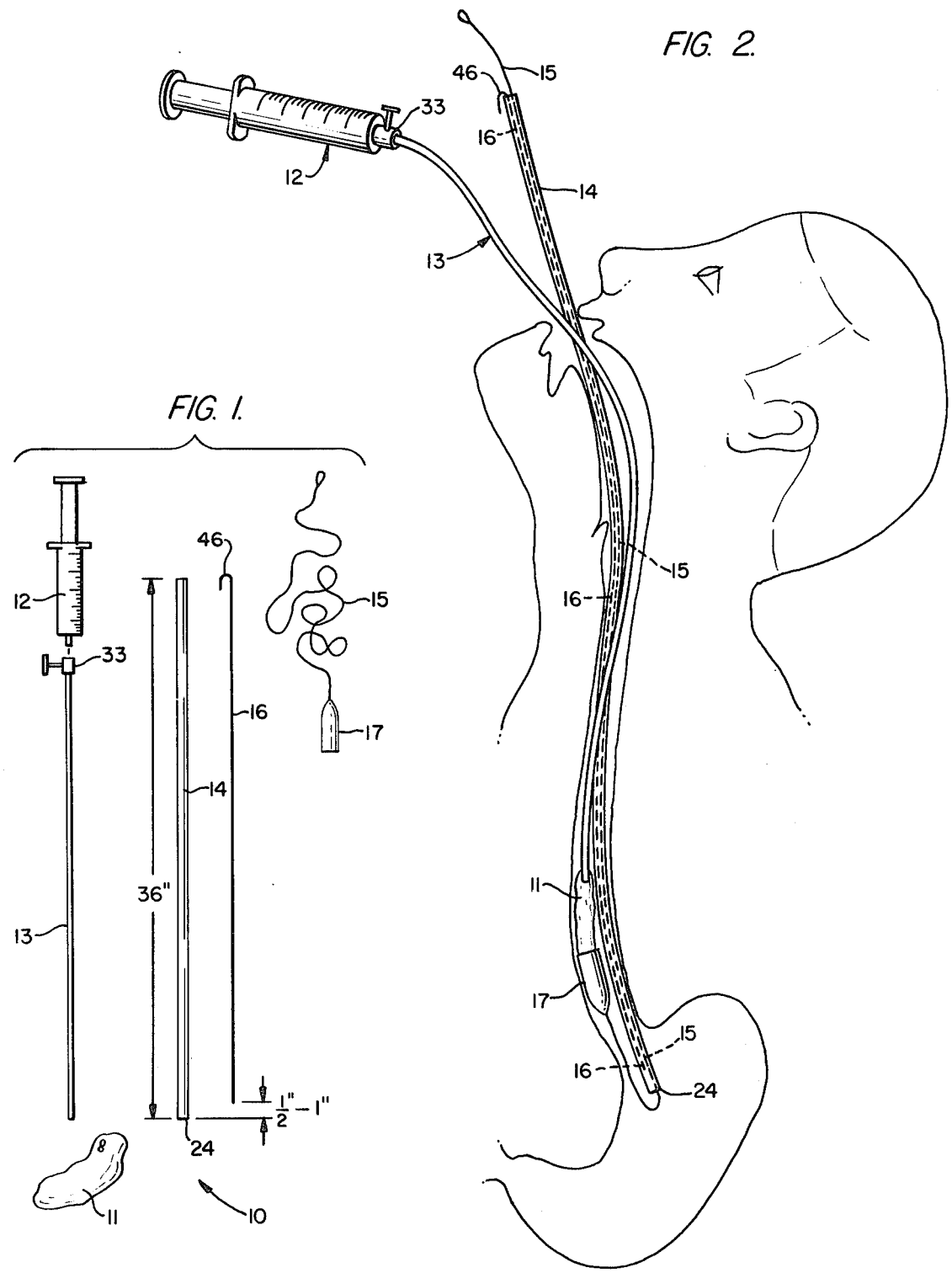

WEIGHT LOSS DEVICE AND METHOD

BACKGROUND OF THE INVENTION

1. Field of the Invention

This invention relates generally to devices for effecting loss of weight in grossly obese human beings. These persons have generally been unable to lose weight by usual, conventional methods, thus requiring that more structured and stringent methods be used.

2. Description of the Prior Art

A common problem with known devices and methods for weight loss of the conventional type is that in most cases they depend upon the will power of the patient (obese person) to achieve the desired results. Many people do not have the necessary strong will to succeed, and therefore failure is the end result.

There have been balloon type devices devised to fit in a person's stomach to create a sensation of "fullness", but often times these are far from effective. Similarly, other type structures for reducing the obese person's stomach volume leave much to be desired. Many require surgical procedures, which always involve some risk.

Existing prior patents which may be pertinent to this invention are as follows: Moreau et al U.S. Pat. No. 3,046,988, July 31, 1962, Berman et al U.S. Pat. No. 4,133,315, Jan. 9, 1979.

U.S. Pat. No. 3,046,988 differs from the present invention because first, the esophageal nasogastric tube is intended to control bleeding from the esophageal varices and not to cause weight loss. Secondly, the esophageal nasogastric tube remains indwelling through the esophagus, nasopharnyx and nose of the patient during the entire time of use. In contrast thereto, the intra-gastric balloon of the present invention is designed to be filled, and then the fill tube is removed, leaving the balloon free-floating in the gastric cavity. Thirdly, the esophageal nasogastric tube of the Moreau et al patent has balloons in the esophagus and in the fundus only of the stomach. The intra-gastric portion of the balloon is small and was never intended to fill the entire gastric volume. While the intra-gastric weight loss system balloon of the present invention occupies the majority of the cavity inside the stomach and conforms to the shape of the stomach. Lastly, patients with an esophageal nasogastric tube in place are unable to take any nourishment by mouth. Patients with the balloon of the present invention are able to eat and drink as before, however, the feeling of fullness occurs after just a small amount of food has been consumed thus, reducing the desire to continue eating by the patient.

The differences between the method and apparatus for reducing obesity of patient U.S. Pat. No. 4,133,315 and the intra-gastric balloon weight loss system of the present invention are: The Berman apparatus is an intra-gastric balloon intended to promote weight loss. However, the balloon remains attached to its fill tube which remains indwelling in the esophagus and out through the nasal passage while in use. This, of course, is quite inconvenient for the patient. The present invention has a removable fill tube, thus leaving the filled balloon free-floating in the gastric cavity. For other than short term use, the Berman apparatus must have the fill tube brought out through a gastrostomy operation (cutting a hole in both the stomach and the abdominal wall). The present invention is intended to be used without surgery of any type. Furthermore, the Berman apparatus is pushed down the esophagus, whereas, the apparatus of the present invention is pulled down the esophagus by a pull-string attached to a standard small nasogastric tube, affording a significant margin of safety.

Another known device uses a stomach compression balloon which is designed to produce weight loss, however, the balloon is placed surgically inside the abdominal peritoneal cavity and outside the gastric (stomach) cavity with a fill tube penetrating the abdominal wall ending in a reservoir buried in the subcutaneous location. This balloon is extragastric and the balloon of the present invention is intra-gastric. Of course, the balloon of this extragastric system requires major surgery for instillation. The balloon and method of the present invention avoids all surgery.

Applicant is aware of still another weight loss system which uses air to inflate a balloon in the patient's stomach. However, when air is used the balloon deflates fairly quickly, usually within a week or so. And, of course, this system can be very dangerous for anyone travelling to a higher altitude after the initial inflation of the balloon.

None of the known prior art devices offers the new and novel features of the present invention.

SUMMARY OF THE INVENTION

An object of the present invention is to provide an apparatus and method for reducing weight in obese humans without any substantial risk because of surgery, and a system which is relatively easy and convenient to use.

Another object of the present invention is to provide an easily installed device for creating the sensation of fullness in an obese patient after only a small amount of food has been eaten in the normal manner. Thus, making it easy for the patient to adhere to a rigid diet, and substantially reduces total food intake.

A further object of this invention is to provide a balloon-type device which can be easily and with a high degree of safety used with an obese person to assist in weight loss thereof.

A still further important object of the present invention is to provide a system of weight loss which is flexible in that it can be used with a conventional type of diet, and thus will help a patient lose weight in a more normal manner than other known type systems.

Another object of the present invention is to provide a balloon type weight loss device which can be placed in a person's stomach through the mouth and esophagus without great discomfort, or risk, and furthermore the structure used to properly place the balloon is entirely removed once the balloon is properly installed so that the balloon alone remains in the stomach.

The present invention has a number of new and novel features. A gastric shaped balloon is placed in the stomach of an obese person desiring to lose weight by a convenient and risk-free structure and method. This method of placing the balloon, the balloon structure itself, and the apparatus used for properly placing the balloon in a person's stomach are all included in the present invention. Also the method of balloon removal at the end of the overall diet system process is believed to be new and unique.

The intra-gastric balloon weight loss system of the present invention includes an intra-gastric elastomeric rubber balloon with self-sealing fill valve, intended to be placed and retrieved without surgery. As a benign space-occupying device, the balloon will decrease gastric capacity to the point that saity (the feeling of fullness) will occur after very little food has been consumed. Most of the advantages of gastric and intestinal by-pass surgery as now practiced for morbid obesity (more than 100 pounds overweight) will be realized, without surgery. And, thus all of the many complications of surgery will be avoided.

The main device of the present apparatus is an elastomeric balloon which is gastric shaped. It is inflated with a liquid, such as saline and X-ray contrast media.

Because after installation of the present device, total food consumption will be markedly reduced, protein, vitamins and mineral supplements should be taken daily and progress should be monitored by a physician weekly. Periodic X-rays can confirm proper presence and position of the balloon in the patient. Habit re-training instruction is preferably given the patient by a tape recorded instructional course which can be listed to while pedaling a stationary bicycle or walking on a treadmill.

After the desired weight of the patient is reached, the balloon is withdrawn by the gastro-enterologist through the esophagus by a gastroscope after perforating the balloon to deflate it. Of course, the liquid released from the balloon passes through the patient in the normal manner without harm.

Follow-up examination and weight monitoring should be continued weekly for several months, then monthly for two years, or so, if the weight loss is to be maintained.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the component parts of the present invention;

FIG. 2 is a side elevational view of the balloon of the present invention being placed in the stomach of an obese patient.

DESCRIPTION OF THE PREFERRED EMBODIMENT

Figure 3:
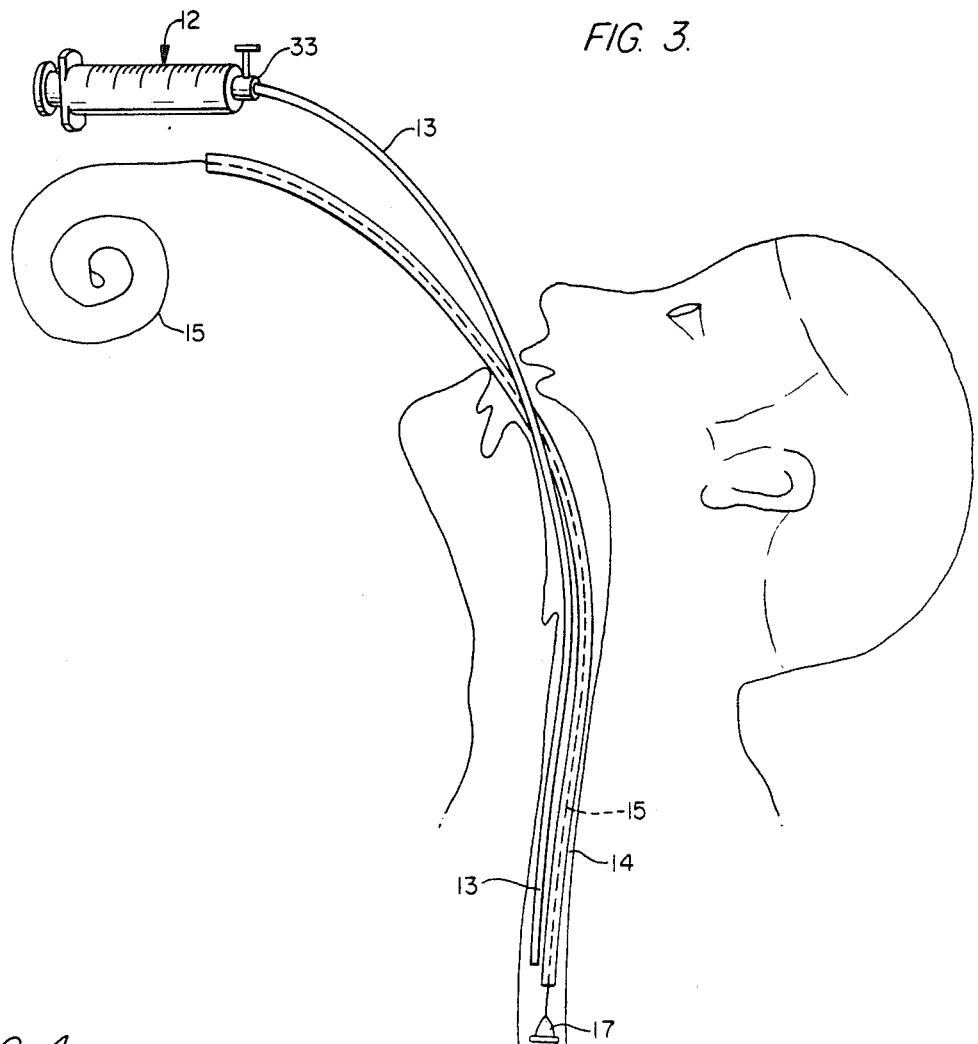
FIG. 3 is a side elevational view of the balloon after placement and inflation thereof, and with the insertion apparatus ready for removal.

Referring to FIG. 1 of the drawings, reference numeral 10 indicates in general the component parts of the weight loss apparatus of the present invention. The deflated and rolled up balloon device is shown in FIG. 2 being placed (pulled) into place in the stomach (gastric cavity) of an obese patient.

The main component parts of the apparatus, as clearly shown in FIG. 1, are the stomach (gastric) shaped, pre-formed balloon 11, the syringe 12 connected to the fill tube 13 by way of a three-way stop cock or valve 33, a flexible hollow naso-gastric (N-G) tube 14, a stiffener rod or wire (stylette) 16, and a pull string 15 having attached at one a finger cot 17.

Preferably, the flexible fill tube 13 is of conventional construction, and the three-way valve 33 is designed so as to permit filling of the syringe 12 with the desired balloon inflation liquid in the conventional manner. The naso-gastric (N-G) tube 14 is also of conventional construction. It is flexible, hollow, and approximately 36" (91.44 cm) long. The stiffener (stylette) 16 has a hook 46 on one end, and is ½" to 1" (1.27 to 2.54 cm) shorter than the N-G tube 14. The hook prevents the stiffener 16 from accidentally being inserted too far into the N-G tube 14, and the shorter length assures that it will not protrude into the patient's stomach.

The pull string 15 (preferably of nylon) with finger cot 17 attached is used, as described below, to place the balloon 11 in the patient's stomach.

Figure 4:
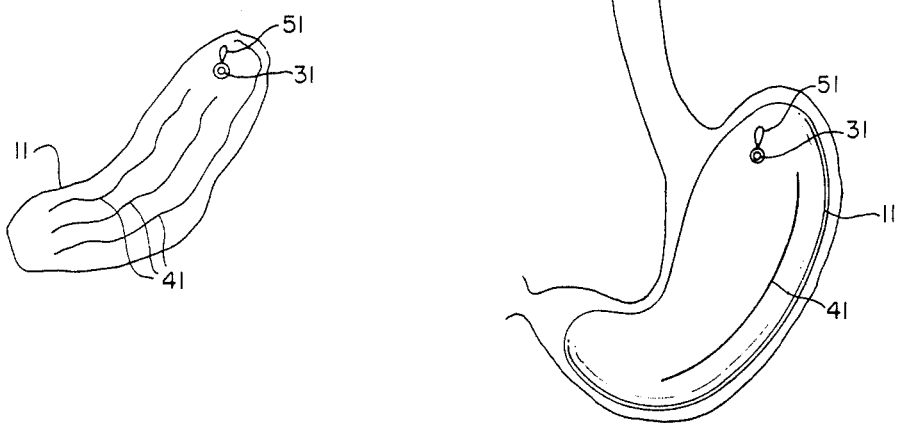
FIG. 4 is a perspective view of the stomach shaped balloon structure per se, as inflated and with X-ray opaque threads and withdrawal loop incorporated therewith.

The balloon 11 (see FIG. 4) is very similar to saline inflatable breast implants as presently manufactured by Wright Dow-Corning, Heyer-Schulte, Medical Engineering and Mammatech. The significant difference is that the device of the present invention is in the shape of a distended human gastric cavity instead of a breast.

Radio-opaque, X-ray marking threads 41 are built into the balloon during the manufacture thereof, so that the position thereof can be readily ascertained through conventional X-ray techniques. Also, a self-closing, liquid retention when closed, fill valve 31 is provided as well as a withdrawal loop 51 for later use in removing the balloon. The balloon 11 is placed in position in a patient's stomach by passing the standard naso-gastric (N-G) tube 14 through the mouth. The N-G tube has the previously placed nylon pull string 15 through the lumen and back up the exterior thereof. After the tip 24 of the tube 14 is confirmed to be in the stomach, the metal stiffener (stylette) 16 is run down the lumen to within 1" of the distal end of the N-G tube. The balloon 11 with the fill tube 13 attached is rolled up and inserted into the rubber finger cot 17 to which the pull string 15 is attached. Then, by pulling the string 15 through the lumen of the N-G tube 14, the balloon containing finger cot 17 is drawn down into the stomach. After confirmation of the placement of the balloon 11 in the stomach the stylette 16 is removed and the balloon 11 is inflated with saline plus contrast media (to make X-ray visualization possible) and Kanamycin (to maintain sterility inside the balloon). Inflation of the balloon causes the finger cot 17 to roll up and remove itself. The balloon 11 is inflated to occupy the majority of the gastric cavity, then the fill tube 13 is withdrawn and the pull-string 15 with the finger cot attached is withdrawn. The self-sealing valve 31 prevents leakage after the fill tube 13 is removed from the balloon.

Because total food consumption will be markedly reduced by use of this device, food supplements including protein, vitamins and minerals should be taken daily and progress must be monitored by a physician weekly. Good eating habit training instruction may be given with a tape recorded instructional course which can be listened to while following a regular exercise program.

When the desired weight has been achieved, the balloon is withdrawn by a gastro-enterologist through the esophagus by a gastroscope after perforating the balloon to deflate it.

Follow-up examination and weight monitoring must be continued for several years thereafter if the weight loss is to be maintained.

The entire intra-gastric balloon weight loss system is much more than just a balloon as can be seen. It comprises 1. The free floating intra-gastric balloon (without tubes attached).
2. The method by which it is placed and filled in a patient's stomach.
3. The protein, vitamin and mineral supplements taken by the patient while losing weight with this apparatus.
4. Eating habit re-training instructional tapes for use by the patient.
5. The process of listening to the tapes while exercising on a stationary bicycle.
6. The method by which the balloon is removed from the patient.
7. The subsequent monitoring of the patient to supervise maintenance of the weight loss long enough for the new eating habit patterns to be firmly entrenched.

The main features of the present invention encompass Items 1 and 2. However, all seven items are an integral part of the overall weight loss system as used with the intra-gastric balloon.

The actual method of placing a balloon 11 in a person's stomach is quick, easy, pain free, and without any surgery. The pull string 15 is passed through the lumen (center) of a standard nasogastric (N-G) tube 14 and back up the outside of the tube. The tube is passed, without the need for general anesthesia, through the mouth, down the esophagus, and, after its presence in the stomach is confirmed, inflated. Inflation is by injecting liquid and listening over the stomach with a stethescope. A stiffener rod or stylette 16 is passed through the lumen of the N-G tube 14 to, but not past, the final one-half inch of the tube 14. The pull string 15 in the lumen of the tube 14 is then pulled, drawing the finger cot 17 containing the collapsed balloon with fill tube attached, through the mouth, down the esophagus and into the stomach. The fill tube is then injected by use of the syringe 12 with a predetermined volume of water, saline, cellulose, gel, food, X-ray contrast media, drugs, antibiotics or any combination of the above. Thus, inflating the balloon which causes the finger cot container to unroll itself off the balloon. After the balloon 11 is filled to a predetermined volume, the nasogastric tube 14 with stiffener 16, pull string 15 and finger cot 17 is withdrawn. Then the fill tube 13 is withdrawn and the self-sealing valve 31 on the balloon closes, leaving the balloon 11 free-floating in the person's gastric cavity with no tubes attached.

Presence of the balloon in the proper position in human being's gastric cavity can be confirmed by X-ray immediately, and periodically, because of a radio-opaque thread incorporated into the construction of the balloon and the volume can be confirmed if the balloon is filled with a radio-opaque media such as Cysto-conray II.

Water, and food supplements including the minimum daily requirement of protein, vitamins and minerals may be recommended or required. Eating habit re-training, instructional tape recorded lessons, suggestions and directions for self-motivation, and self-hypnotism, may be recommended or required for self-motivation, and self-hypnotism, may be recommended or required multiple times daily and when falling asleep at night. Aerobic exercise while listening to the tapes may be recommended or required a minimum of three times per week while the patient is under treatment and during maintenance.

The balloon may be removed when the fat loss goal has been achieved or any time before or after that time, *without surgery* and without the need for general anesthesia. The method of removal is by gastroscopy, perforation of the balloon, and by aspiration of the contents thereof, then forceps are used for grasping and/or snaring of the attached withdrawal loop. Then withdrawal of the balloon is effected through the esophagus in the same manner in which the gastroscope is withdrawn.

After balloon removal, follow-up examination, eating habits and weight monitoring may be continued weekly for several months and then monthly for two or more years, if necessary, to maintain the weight loss.

In summary, the present invention includes a free floating intragastric balloon which will help overweight users lose weight. This benign, space occupying device will decrease the gastric capacity to the point that saiety (the feeling of fullness) will occur after very little food has been consumed.

The balloon is designed to occupy the majority of the available intragastric space and float freely in the gastric cavity. It may act as a ball valve obstruction to gastric drainage. After the fill tube is withdrawn and the self-sealing valve closes, there are no tubes left attached and no tubes remain in the esophagus or nasopharnyx. This device can be placed in an awake patient in the same manner as a orogastric tube is passed without the need for surgery or general anesthesia, although it may be passed under anesthesia according to the patient's preference.

The balloon may be inflated with water, saline, cellulose, gel, food, X-ray contrast media or any combination of the above and it may contain pharmacologically active drugs for sustained release or other administration. The volume may be adjusted at any time by reinserting the swallowed fill tube into the self-sealing valve under gastroscopy. If the balloon should suffer a spontaneous deflation, it could be passed through the intestines physiologically or it could be regurgitated without harm to the user. Radio-opaque thread incorporated into the construction of the balloon would identify its position in the gastrointestinal tract.

Water, protein, carbohydrate, fat, vitamins and mineral supplements may be recommended or required while the user is losing weight. Eating habit re-training, instructional tape recorded lessons, suggestions and directions for self-motivation and self-hypnotism may be recommended or required while the user is under treatment. Aerobic exercise while listening to the instructional and motivational tapes for a minimum of fifteen minutes, three times per week, would be recommended or required while the user is under treatment and under maintenance.

The device may be removed at any time without surgery and without the need for general anesthesia by gastroscopy, perforation of the balloon, aspiration of the contents and forceps grasping or snaring the attached withdrawal loop, then withdrawal through the esophagus in the same manner in which the gastroscope is withdrawn.

The intragastric balloon weight loss system is a method for weight loss in overweight patients in which a collapsed, free-floating intragastric balloon with filler tube attached is rolled up inside a rubber finger cot to which a pull string is attached, and thus placed without surgery of any type.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed is:

1. Apparatus for use in achieving a loss of weight in an overweight person comprising:
    an inflatable device;
    means for placing said device within the stomach of the person without surgery;
    additional means for inflating said device with liquid after it has been placed in the person's stomach;
    further means for allowing both said placing means and said inflating means to be completely removed from the person so as to leave the inflated device floating in the person's stomach; and said further means including
        a pull string having a rollable finger cot attached at one end, and a releasable, self-closing fill valve as part of the inflatable device.

2. Apparatus as set forth in claim 1, wherein said releasable, self-closing fill valve receives one end of a flexible fill tube prior to the device being rolled up and associated with the extended finger cot for placing of the inflatable device in the person's stomach, said fill tube being connected to liquid supply means so that the inflatable device can be inflated with liquid after it has been placed in the person's stomach, and such inflation in turn effecting rolling up and disengagement of said finger cot from the device.

3. The method of placing a gastric cavity filling device within an obese person's gastric cavity without any surgery, comprising the steps of:
    providing an inflatable device in deflated form;
    attaching a fill tube to the inflatable device;
    inserting a hollow tube containing a string therethrough into the person's mouth, esophagus and gastric cavity;
    releasably attaching the deflated device with fill tube attached to one end of the string;
    pulling the other end of the string to pull the deflated device into the person's gastric cavity;
    inflating the deflated device through the fill tube and after suitable inflation of the device;
    removing all the placing apparatus so that the inflated device remains free-floating in the person's gastric cavity without any attachments thereto.

4. The method of claim 3, with the further steps of:
    inserting a stiffener member into the hollow tube containing the string therethrough prior to the step of pulling the string.

5. The method of claim 4, with the additional step of using liquid containing an X-ray opaque substance therein for inflating the device.

* * * * *